US011642308B2

(12) United States Patent
Leeah et al.

(10) Patent No.: US 11,642,308 B2
(45) Date of Patent: May 9, 2023

(54) READY TO USE LIQUID FORMULATION

(71) Applicant: QuVa Pharma, Inc., Sugar Land, TX (US)

(72) Inventors: Travis A. Leeah, Sugar Land, TX (US); Jianping Chen, Sugar Land, TX (US); Lijie Zhao, Houston, TX (US)

(73) Assignee: QUVA PHARMA, INC., Sugar Land, TX (US)

( * ) Notice: Subject to any disclaimer, the term of this patent is extended or adjusted under 35 U.S.C. 154(b) by 316 days.

(21) Appl. No.: 17/147,953

(22) Filed: Jan. 13, 2021

(65) Prior Publication Data

US 2021/0251888 A1    Aug. 19, 2021

Related U.S. Application Data

(60) Provisional application No. 62/971,348, filed on Feb. 7, 2020.

(51) Int. Cl.
*A61K 9/00*     (2006.01)
*A61K 31/167*   (2006.01)
*A61K 31/137*   (2006.01)
*A61K 47/02*    (2006.01)
*A61K 47/18*    (2017.01)
*A61K 47/20*    (2006.01)
*A61K 47/12*    (2006.01)

(52) U.S. Cl.
CPC .......... *A61K 9/0019* (2013.01); *A61K 31/137* (2013.01); *A61K 31/167* (2013.01); *A61K 47/02* (2013.01); *A61K 47/12* (2013.01); *A61K 47/183* (2013.01); *A61K 47/20* (2013.01)

(58) Field of Classification Search
CPC .. A61K 9/0019; A61K 31/137; A61K 31/167; A61K 47/02; A61K 47/12; A61K 47/183; A61K 47/20
USPC ....................................................... 514/626
See application file for complete search history.

(56) References Cited

U.S. PATENT DOCUMENTS 8,628,805 B2     1/2014  Baillie et al.
10,952,962 B1 *  3/2021  Leeah ................. A61K 31/137

FOREIGN PATENT DOCUMENTS

GB          425678 A      3/1935
WO      2019/072723 A1    4/2019

OTHER PUBLICATIONS

Bernards et al., Effect of Epinephrine on Lidocaine Clearance In Vivo, Anesthesiology (1999) 91(4): 962-968 ("Bernards").
Bonhomme et al., Chemical Stability of Lignocaine (Lidocaine) and Adrenalin (Epinephrine) in pH-adjusted Parenteral Solutions, J. Clin. Pharm. Thera. (1988) 13(4): 257-261 ("Bonhomme").
Christoph et al., Pain Reduction in Local Anesthetic AdminisliaLion through pH Buffering, Ann. Emerg. Med. (1988) 17(2): 117-120 ("Christoph").
Connors et al., Chemical Stability of Pharmaceuticals: A Handbook for Pharmacists, 2nd Ed. (1986), pp. 438-448 ("Connors").
Edgepharma Product Page edgepharma.com/products/dermatology/buffered-lidocaine/, last accessed on Jan. 10, 2020.
Flynn, G.L., Buffers—pH Control within Pharmaceutical Systems, J. Parenteral Drug Assoc. (1980) 34(2): 139-162 ("Flynn").
Fresenius Kabi Dear Customer Letter, Nov. 14, 2016.
Hajratwala B.R., Sulfite Induced Anaerobic Degradation of Epinephrine in Lidocaine Hydrochloride Injection, Drug Development and Industrial Pharmacy (1977) 3(1): 65-72.
Hajratwala, B.R., Kinetics of Sulfite-Induced Anaerobic Degradation of Epinephrine, J. Pharm. Sci. (1975) 64(1): 45-48.
Handbook of Pharmaceutical Excipients, Edetic Acid, 5th Ed., pp. 260-263, Eds. Rowe et al. (2006) ("Handbook").
Hinshaw et al., Preparation of pH-adjusted Local Anesthetics, Ophthalmic Surg. (1995) 26(3): 194-199 ("Hinshaw").
Kennedy et al., The "Ouchless Emergency Department", Pediatric Clinics of North America (1999) 46(6): 1215-1247 ("Kennedy").
Larson et al., Stability of Buffered Lidocaine and Epinephrine Used for Local Anesthesia, Dermatol. Surg. (1991) 17(5): 111-414 ("Larson").
Long et al., Taking the 'sting' out of Local Anaesthetics, Brit. J. Dermatol. (1991) 125(5): 452-455 ("Long").
Abstract of Maloney et al., Iontophoretic Administration of Lidocaine Anesthesia in Office Practice: An Appraisal, J. Dermatol. Surg. Oncol. (1992) 18(11): 937-940 ("Maloney").
Murakami et al., Buffered Local Anesthetics and Epinephrine Degradation, J. Dermatol. Surg. (1994) 20(3): 192-195 ("Murakami").
Prescribing information for EMPI's Lidocaine HCI 2% and Epinephrine 1:100,000 Solution for Topical Iontophoretic System ("EMPI's Iontophoretic System"). 2004.
Robinson et al., Chemical stability of bupivacaine, lidocaine and epinephrine in pH-adjusted solutions, Anaesthesia (2000) 55(9): 853-858 ("Robinson").
Sinnott et al., On the Mechanism by Which Epinephrine Potentiates Lidocaine's Peripheral Nerve Block, Anesthesiology (2003) 98(1): 181-188 ("Sinnott").
Stewart, et al., Neutralized Lidocaine with Epinephrine for Local Anesthesa-II, J. Dermatol Surg Oncol (1990) 16(9); 842-845 ("Stewart").
Xylocaine® (lidocaine HCI and epinephrine Injection, USP), Nov. 2018 ("Xylocaine® Label").
Copending U.S. Appl. No. 16/381,407, filed Apr. 11, 2019 entitled "Ready to use Liquid Formulation".

\* cited by examiner

*Primary Examiner* — Kristin A Vajda
(74) *Attorney, Agent, or Firm* — Merchant & Gould P.C.; Daniel R. Evans

(57) ABSTRACT

Disclosed herein is a ready-to-use liquid, injectable formulation comprising lidocaine and epinephrine. Also disclosed herein is a process for preparing a ready-to-use liquid formulation comprising lidocaine and epinephrine, as well as methods for using the ready-to-use liquid formulation.

20 Claims, No Drawings

READY TO USE LIQUID FORMULATION

RELATED APPLICATION

The present application claims priority to U.S. Provisional Patent Application No. 62/971,348, filed on Feb. 7, 2020, the subject matter of which is incorporated by reference in its entirety.

FIELD OF THE INVENTION

Disclosed herein is a ready-to-use liquid, injectable formulation comprising lidocaine and epinephrine. Also disclosed herein is a process for preparing a ready-to-use liquid formulation comprising lidocaine and epinephrine, as well as methods for using the ready-to-use liquid formulation.

BACKGROUND

Lidocaine with epinephrine 1:100,000 in water (saline) is an anesthetic solution used for local or regional anesthesia by: infiltration techniques such as percutaneous injection, peripheral nerve block techniques such as brachial plexus and intercostal, and central neural techniques such as lumbar and caudal epidural blocks. See e.g., Bernards. The addition of epinephrine provides several distinct advantages to a peripheral nerve block from a clinical standpoint. The advantage of using epinephrine is twofold. First, it reduces the lidocaine plasma concentration (systemic absorption) and thus minimizes the possibility of systemic toxicity. Second, it improves the quality and prolongs the duration of peripheral nerve blocking action of the lidocaine. The mechanism of action is the epinephrine mediates this prolongation of lidocaine action by its vasoconstrictive actions. As a result, one can use a lower concentration of lidocaine (i.e., 0.5% vs 1%) for nerve block.

Many hospitals use lidocaine with epinephrine to provide local anesthesia. The added epinephrine localizes the lidocaine in the in the tissue, thereby decreasing its clearance. See e.g., Sinnott. Despite the fact that epinephrine undergoes decomposition in the presence of sodium metabisulfite (Hajratwala (1975)), most manufactured lidocaine with epinephrine injection products contain sodium metabisulfite at 0.5 mg-1 mg/mL, and some products may include citric acid. See the Xylocaine® Label. Multi-dose vials may include methylparaben (1 mg/mL) or other agents as antimicrobial preservative(s). The pH is adjusted to 4.5 (3.3-5.5). Larson at 412; Hinshaw at 198. The selected pH range of 3.3 to 5.5 serves to minimize precipitation (e.g., by solubilizing lidocaine) and to prolong shelf life (e.g., stabilize epinephrine). Hinshaw at 198.

At pH values of 3.3 to 5.5, lidocaine is present in its cationic form because the lidocaine pKa is about 7.5 to 7.9. Christoph at 118. Lidocaine free base is poorly soluble in water. A preparation having a higher pH increases the fraction of lidocaine free base, and thus, increases the likelihood of a lidocaine-containing precipitate.

Epinephrine racemization rates increase at pH less than about 3.3 and epinephrine oxidation rates increase at pH greater than about 5.5. Connors at 445. However, for this formula to keep epinephrine stable (at this pH), the headspace within the vial must be nitrogen gassed (remove oxygen).

Some patients may experience discomfort (e.g., pain due to stinging/burning) when injected with a lidocaine with epinephrine preparation. See Christoph and Kennedy. Indeed, Long suggests that several factors influence the discomfort associated with injectable anesthetics, such as size of the needle gauge, dermal status, and type of injection (viz., dermal or subcutaneous). Long also suggests that the burning sensation associated with an injection of lidocaine with epinephrine relates to the acidity of said preparations. Some clinicians suggest that pain associated with injection of a lidocaine with epinephrine preparation may be reduced using an iontophoretic system. See e.g., Maloney; see also EMPI's Iontophoretic System.

Previous reports (viz., Christoph, Larson, and Long) suggest that neutralization of a commercial lidocaine with epinephrine preparation using sodium bicarbonate may ameliorate the discomfort associated with injection. The reported results show that pH-adjustment to a physiological pH results in a preparation having accelerated epinephrine degradation. See Larson and Murakami. Epinephrine degradation at physiological pH is not surprising considering the pH-profile for epinephrine stability. See e.g., Connors at 445. For instance, Robinson reports that pH-adjustment results in substantial loss of epinephrine after 24-hours. Christoph recommends immediate use of pH-adjusted lidocaine with epinephrine, while Stewart recommends discarding pH-adjusted lidocaine with epinephrine within 1-week after preparation. Larson recommends discarding refrigerated, pH-adjusted lidocaine with epinephrine 2-weeks after preparation. Additionally, Hinshaw does not recommend pH-adjustment (based on fixed volume pH-adjustment using sodium bicarbonate) because of the complications associated with particulate formation. As mentioned by Larson, "[i]n a high-volume surgery clinic, buffering the local anesthetic at the time of surgery is inconvenient and introduces potential mixing error." Larson at 414.

Buffered lidocaine with epinephrine is not available commercially generally due to stability issues with both lidocaine and epinephrine in a buffered state. The issue is the immediate degradation of epinephrine when in contact with buffers. Edge Pharma (a 503B outsourcing facility) provides a buffered lidocaine with epinephrine having limited stability (BUD of 30 days refrigerated). See Edge Pharma Product Page. Edge Pharma's buffered lidocaine epinephrine contains phosphate buffer. As a point of reference, USP <797> defines the Beyond-Use Date (or BUD) as the date or time after which a compounded sterile formulation may not be stored or transported and is calculated from the date or time of compounding. Hajratwala (1977) evaluated the stability of epinephrine in a buffered lidocaine with epinephrine preparation. Therein, Hajratwala (1977) disclosed a preparation containing 1% lidocaine, 0.001% epinephrine, 0.05% sodium metabisulfite, 0.1% methyl paraben, 0.03 M acetate buffer to adjust a pH to 4.4, and sufficient sodium chloride to adjust isotonicity.

In view of the foregoing, an objective of the disclosure relates to a ready-to-use liquid, injectable formulation comprising lidocaine and epinephrine that has reduced discomfort with injection and that has a shelf life of 60 to 90 days when stored at about 5° C.

DETAILED DESCRIPTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not.

Embodiment 1. A ready-to-use liquid formulation comprising: lidocaine hydrochloride in an amount of about 5 mg/mL or about 10 mg/mL; epinephrine in an amount that ranges from about 10 mcg/mL to about 10.8 mcg/mL; sodium chloride in an amount of about 6 mg/mL to about 7 mg/mL; sodium metabisulfite in an amount of about 5 mcg/mL to about 5.6 mcg/mL; EDTA sodium in an amount of about 0.5 to about 0.6 mg/mL; optionally N-acetyl-L-cysteine in an amount of about 10 mcg/mL to about 13 mcg/mL; citrate buffer in an amount of about 1 to about 10 mM; a sufficient amount of sterile water for injection; and a sufficient amount of a pH adjuster to obtain a pH that ranges from about 6.3 to about 6.4; wherein the epinephrine content ranges from about 9 mcg/mL to about 9.7 mcg/mL after storage in a light protected environment for about 60 days to about 90 days at a temperature of about 5° C.

It is understood that the epinephrine content ranging from about 9 mcg/mL to about 9.7 mcg/mL after storage at about 5° C. for about 60 days to about 90 days is determined by UPLC, as explained elsewhere, where the period refers to the time of preparation until from about 60 days to about 90 days. For an epinephrine labeled content of about 10 mcg/mL, an epinephrine content ranging from about 9 mcg/mL to about 9.7 mcg/mL after storage at about 5° C. for about 60 days to about 90 days represents about 90% to about 97% of epinephrine labeled content.

It also is understood that EDTA sodium may be obtained from EDTA disodium dihydrate or from EDTA (viz., Edetic acid). The reported acid dissociation constants for EDTA are pKa1=2.00; pKa2=2.67; pKa3=6.16; and pKa4=10.26. Handbook at 261. Accordingly, one will appreciate that EDTA sodium may be comprised of EDTA having differing ionization states depending on the pH of the formulation. Thus, the expression "EDTA sodium" refers EDTA disodium dihydrate, as well as the EDTAs of differing ionization states.

Embodiment 2. The ready-to-use liquid formulation of Embodiment 1, wherein N-acetyl-L-cysteine is present in an amount of 10 mcg/mL to about 13 mcg/mL.

Embodiment 3. The ready-to-use liquid formulation of Embodiment 1, wherein epinephrine is present in an amount of about 10 mcg/mL and the sodium metabisulfite in an amount of about 5 mcg/mL.

Embodiment 4. The ready-to-use liquid formulation of Embodiment 1, wherein epinephrine is present in an amount of about 10.5 mcg/mL and the sodium metabisulfite in an amount of about 5.4 mcg/mL.

Embodiment 5. The ready-to-use liquid formulation of Embodiment 1, wherein epinephrine is present in an amount of about 10.8 mcg/mL and the sodium metabisulfite in an amount of about 5.6 mcg/mL.

Embodiment 6. A syringe containing about 3 mL to about 5 mL of the ready-to-use liquid formulation of any one of Embodiments 1-5. The syringe may be a syringe available commercially by Becton, Dickinson and Company. BD syringes may be fitted with a Luer-Lok tip and have volumes (in mL) of: 1, 3, 5, 10, 20, 30, and 60.

Embodiment 7. A light-sensitive container comprising the syringe of Embodiment 6, wherein the light sensitive container has light transmission of less than 5%, less than 4%, less than 3%, less than 2%, or less than 1% at any wavelength between 290 nm and 450 nm. Said light-resistant container may comprise, for example, an amber-colored bag, film, or plastic.

Embodiment 8. A ready-to-use liquid formulation consisting of: lidocaine hydrochloride in an amount of about 5 mg/mL or about 10 mg/mL; epinephrine in an amount that ranges from about 10 mcg/mL to about 10.8 mcg/mL; sodium chloride in an amount of about 6 mg/mL to about 7 mg/mL; sodium metabisulfite in an amount of about 5 mcg/mL to about 5.6 mcg/mL; EDTA sodium in an amount of about 0.5 mg/mL to about 0.6 mg/mL; optionally N-acetyl-L-cysteine in an amount of about 10 mcg/mL to about 13 mcg/mL; citrate buffer in an amount of about 1 to about 10 mM; a sufficient amount of sterile water for injection; and a sufficient amount of a pH adjuster to obtain a pH that ranges from about 6.3 to about 6.4; wherein the epinephrine content ranges from about 9 mcg/mL to about 9.7 mcg/mL after storage in a light protected environment for about 60 days to about 90 days at a temperature of about 5° C.

It is understood that the epinephrine content ranging from about 9 mcg/mL to about 9.7 mcg/mL after storage for about 60 days to about 90 days is determined by UPLC, as explained elsewhere, where the period refers to the time of preparation until from about 60 days to about 90 days.

Embodiment 9. The ready-to-use liquid formulation of Embodiment 8, wherein N-acetyl-L-cysteine is present in an amount of 10 mcg/mL to about 13 mcg/mL.

Embodiment 10. The ready-to-use liquid formulation of Embodiment 8, wherein epinephrine is present in an amount of about 10 mcg/mL and the sodium metabisulfite in an amount of about 5 mcg/mL.

Embodiment 11. The ready-to-use liquid formulation of Embodiment 8, wherein epinephrine is present in an amount of about 10.5 mcg/mL and the sodium metabisulfite in an amount of about 5.4 mcg/mL.

Embodiment 12. The ready-to-use liquid formulation of Embodiment 8, wherein epinephrine is present in an amount of about 10.8 mcg/mL and the sodium metabisulfite in an amount of about 5.6 mcg/mL.

Embodiment 13. A syringe containing about 3 mL to about 5 mL of the ready-to-use liquid formulation of any one of Embodiments 8-12. The syringe may be a syringe available commercially by Becton, Dickinson and Company. BD syringes may be fitted with a Luer-Lok tip and have volumes (in mL) of: 1, 3, 5, 10, 20, 30, and 60.

Embodiment 14. A light-sensitive container comprising the syringe of Embodiment 13, wherein the light sensitive container has light transmission of less than 5%, less than 4%, less than 3%, less than 2%, or less than 1% at any wavelength between 290 nm and 450 nm. Said light-resistant container may comprise, for example, an amber-colored bag, film, or plastic.

Embodiment 15. A method for providing procedural analgesia to a patient in need thereof, which comprises: administering the ready-to-use liquid formulation of Embodiment 1 or Embodiment 8 to the patient.

Embodiment 16. The method of Embodiment 15, wherein the procedural analgesia is associated with a venipuncture, a shave removal, or a punch biopsy.

Embodiment 17. A process for preparing the ready-to-use liquid formulation of Embodiment 1 or of Embodiment 8, which comprises: a) dissolving lidocaine HCl, sodium chloride, sodium citrate, and citric acid in a first container including sterile water for injection to obtain a first solution; b) dissolving EDTA sodium in second container including sterile water for injection to obtain a second solution and adjusting the pH thereof to a value of from about 2.6 to about 2.7; c) dissolving epinephrine in the pH-adjusted solution from step b) and optionally adjusting the pH to a value of from pH 2.6 to about 2.7; d) dissolving epinephrine in the second container of step c); e) optionally, adjusting the pH of the solution of step c) to a value of from about 2.6 to about 2.7; f) dissolving sodium metabisulfite and, optionally, N-Acetyl-L-cysteine in the second container of step e); g) transferring the solution of step f) to the first container; h) optionally, adjusting the pH of the solution in the first container of step g) to a obtain a pH that ranges from about 6.3 to about 6.5; and h) filtering the solution of step h) through a 0.22 micron filter.

It will be understood that variations (or additional details) may be performed with respect to the process of Embodiment 17, see e.g., Examples 1 and 2, disclosed herein.

It is understood that the process for preparing the ready-to-use liquid formulation disclosed and claimed herein does not utilize deoxygenated sterile water for injection. Further, no precautions are taken to exclude oxygen (viz., $O_2$) from the containers and syringes that contain the ready-to-use liquid formulation. Thus, one will appreciate that the ready-to-use liquid formulations disclosed and claimed herein further comprise a dissolved amount of oxygen. With the understanding that oxygen solubility in water is about 40 mg/L ($\approx$25° C. and $\approx$1 bar), the ready-to-use liquid formulations disclosed and claimed herein may further comprise about 40 mg/L of oxygen.

Embodiment 18. A syringe product containing about 5 mL of the ready-to-use liquid formulation prepared by the process of Embodiment 17.

Embodiment 19. The syringe of Embodiment 18, wherein each of lidocaine and epinephrine has a potency of at least 90% after storage for about 3-months at a temperature of about 25° C.

Embodiment 20. A light-sensitive container comprising the syringe of Embodiment 18, wherein the light-sensitive container has a light transmission of less than 5% at any wavelength between 290 nm and 450 nm.

In an aspect of the first through twentieth embodiments, the citrate buffer is present in an amount of about 1 mM, about 2 mM, about 3 mM, about 4 mM, about 5 mM, about 6 mM, about 7 mM, about 8 mM, about 9 mM, or about 10 mM. In another aspect of the first through twentieth embodiments, the citrate buffer is present in an amount of about 5 mM. The citrate buffer may comprise citric acid, dihydrogen citrate or a pharmaceutically acceptable salt thereof, monohydrogen citrate or a pharmaceutically acceptable salt thereof, tribasic citrate or a pharmaceutically acceptable salt thereof, and a combination thereof. The citrate species may be sodium dihydrogen citrate, sodium monohydrogen citrate, potassium dihydrogen citrate, potassium monohydrogen citrate, and the like.

Aspects of the ready-to-use liquid, injectable formulation are exemplified below. The exemplified embodiments should not be used to limit the scope of the claimed subject matter.

EXAMPLES

BD syringes described herein are available commercially from Becton, Dickinson and Company. The BD syringes may be fitted with a Luer-Lok tip and have volumes (in mL) of: 1, 3, 5, 10, 20, 30, and 60.

Ultra Performance Liquid Chromatography (UPLC) was used for purposes of identification and potency determinations.

| | Epinephrine |
|---|---|
| Equipment: | Waters Acquity H Class UPLC with UV Detector (or equivalent) |
| Column: | Luna 5 μm C18(2) 100A, 150 × 4.6 mm column |
| Column Temperature: | 50.0° C. |
| Flow Rate: | 1.0 mL/min |
| Injection Volume: | 10 μL |
| UV Detector: | 220 nm |
| Run Time: | 17 minutes |
| Seal Wash, Purge, and Wash: | Water:Acetonitrile (50:50) |
| Mobile Phase A: | pH 3.0 buffer |
| Mobile phase B: | Acetonitrile |
| Gradient: | 0 min: 90% A \| 10% B |
| | 5 min: 70% A \| 30% B |
| | 14 min: 70% A \| 30% B |
| | 14.5 min: 90% A \| 10% B |
| | 17 min: 90% A \| 10% B |

Mobile Phase A (pH 3 buffer) is prepared by dissolving 3.0 g of 1-Heptanesulfonic acid Sodium Salt in 1000 mL of purified water and mix well. Adjust the pH of the buffer with Phosphoric acid to pH3.0±0.1.

"Diluent" (about 0.001 NHCl in purified water) is prepared by adding 1.0 mL of 1N Hydrochloric Acid to 1000 mL of purified water with thorough mixing.

Potency assays used working standard solutions for Lidocaine HCl and Epinephrine Bitartrate. Use low actinic glassware and protect solutions from light.

Epinephrine bitartrate working standard solution is prepared by: (i) accurately weighing 20.0 mg of Epinephrine Bitartrate USP standard, (ii) transferring the standard into 100.0 mL volumetric flask using 50 mL of Diluent, (iii) sonicating for 5 minutes and cooling to room temperature, and (iv) diluting to volume with Diluent. The concentration of Epinephrine Bitartrate in the standard solution is about 0.2 mg/mL, which corresponds to an epinephrine concentration of about 0.1 mg/mL. The exact concentration is based on the weight of weighed USP standard.

Lidocaine working standard solution is prepared by: (i) accurately weighing about 25 mg of Lidocaine HCl USP (or about 23 mg of Lidocaine USP) standard, (ii) transferring the standard into a 25.0 mL volumetric flask and adding 1 mL 1 N HCl solution, (iii) sonicating for about 5 minutes, and (iv) diluting to volume with purified water followed by mixing.

The concentration of Lidocaine HCl in the working standard solution is about 1.0 mg/mL for Lidocaine HCl, which corresponds to about 0.9 mg/mL for Lidocaine. The exact concentration is based on the weight of weighed USP standard.

Epinephrine and Lidocaine working standard solution ("Epi/Lido WSS") is prepared by: (i) transferring 5.0 mL of epinephrine bitartrate working standard solution to a 50 mL volumetric flask, (ii) transferring 5.0 mL of lidocaine working standard solution to the 50 mL volumetric flask, and (iii) diluting to volume with 0.001 N HCl with thorough mixing. The concentration of Epinephrine Bitartrate in the Epi/Lido WSS is about 20 mcg/mL, while the concentration of Epinephrine is about 10 mcg/mL. The concentration of Lidocaine HCl in the Epi/Lido WSS is about 0.1 mg/mL, which corresponds to about 0.09 mg/mL for lidocaine.

Samples (or formulations) described herein are used to prepare analytical samples for determining lidocaine and epinephrine potencies. The analytical samples were prepared from intermediate samples. The intermediate samples were prepared by: (i) transferring 5.0 mL of sample (or formulation) into a 50 mL volumetric flask and (ii) diluting to volume with 0.001 N HCl with thorough mixing. Analytical samples were prepared by: (i) transferring 5 mL of sample (or formulation, e.g., 0.5% lidocaine with epinephrine ("lido w/epi") or 1.0% lido w/epi) to a suitable volumetric flask (viz., 25 mL for 0.5% lido w/epi or 50 mL for 1.0% lido w/epi) and (ii) diluting with Diluent. As a point of reference, the dilution factors are 5 for the 0.5% lido w/epi analytical sample and 10 for the 1.0 lido w/epi analytical sample.

Calculate the potency of Lidocaine HCl as follows:

$$\text{Lidocaine HCl Potency}(\%) = \frac{As}{Astd} \times C \times DF \times \frac{P}{100} \times CF \times \frac{1}{LC} \times 100$$

Where
As is the UPLC peak area of lidocaine (elution time of about 9.3 min), from analytical samples (N=NMT 10);
Astd is the average UPLC peak area (N=5) of Epi/Lido WSS;
C is the working standard concentration of Lidocaine HCl or Lidocaine in Epi/Lido WSS (about 0.1 mg/mL for Lidocaine HCl (or about 0.09 mg/mL for Lidocaine);
DF is a dilution factor (e.g., DF is 5 for the 0.5% lido w/epi analytical sample and 10 for the 1.0 lido w/epi analytical sample);
P is the Standard potency, % (obtained by comparison to standard solution);
CF is the correction factor (CF=1 when Lidocaine HCl standard is used and CF=1.1556 when the lidocaine standard is used, where CF=1.1556 is the ratio of the molecular weight of Lidocaine HCl (270.80) to the molecular weight of Lidocaine (234.34); and
LC is the Label Claim of the Lidocaine HCl in the LE composition, e.g., 5 mg/mL or 10 mg/mL.

Calculate the Potency of Epinephrine as Follows:

$$\text{Epinephrine Potency}(\%) = \frac{As}{Astd} \times C \times \frac{P}{100} \times DF \times \frac{1}{LC} \times CF \times 100$$

Where
As is the UPLC peak area of epinephrine (elution time of about 4.8 min);
Astd is the average UPLC area (N=5) of epinephrine from working standard solution;
C is the epinephrine concentration (about 10 mcg/mL) in Epi/Lido WSS;
P is the standard potency, % (obtained by comparison to standard solution);
DF is the dilution factor (e.g., DF is 5 for the 0.5% lido w/epi analytical sample and 10 for the 1.0 lido w/epi analytical sample);
CF is the correction factor (0.54969), which is the ratio of the molecular weight of epinephrine (183.207) to the molecular weight of epinephrine bitartrate (333.29); and
LC is the Label Claim of the Epinephrine in the sample (or formulation), 10 mcg/mL.

Pre-formulation evaluations were performed to identify a lidocaine with epinephrine formulation with reduced pain upon injection that was stable for 60 to 90 days. All available buffers that were safe for use in parenteral injections were evaluated. Next, different stabilizers, chelating agents, and preservatives were evaluated for the purpose of assessing stability.

To assess robustness of the buffer combinations with stabilizers, the pre-formulation evaluations included forced degradations studies, including storage at about 40° C. conditions. The pre-formulation samples that exhibited robustness were evaluated further under storage of room temperature and refrigerated conditions.

Various molar buffer concentrations were evaluated from <10 mM up to 20 mM. Prior investigations suggest that buffers above 10 mM may contribute to pain on injection with a subcutaneous injection. Since the pain on injection is believed to be pH related, the goal was to evaluate pH-values that range from about 5.5 to about 7.0. The following components (buffers, stabilizers, and preservatives) were evaluated: Sodium Bicarbonate, Disodium Phosphate, Sodium Citrate/Citric Acid, Disodium EDTA, Formaldehyde (as its sodium bisulfite adduct), Ascorbic Acid, L-Cysteine, N-Acetyl-L-Cysteine, Sodium metabisulfite, and Sodium Bisulfite.

A first study of epinephrine potency occurred for two sets of pre-formulation samples containing either 0.5% w/v lidocaine hydrochloride (HCl) with epinephrine or 1.0% w/v lidocaine HCl with epinephrine. The first study evaluated epinephrine potency at varying pH-values (viz., ≈5.5, ≈6.0, ≈6.5, ≈7.0), and varying concentrations of citrate buffer (≈5 mM or ≈10 mM) and EDTA sodium (≈0.2 mg/mL and ≈0.6 mg/mL). Samples were prepared as described herein and stored under refrigerated conditions (about 5° C.) and protected from light. Lidocaine and epinephrine potencies were evaluated by UPLC.

Table 1a summarizes the compositional makeup and epinephrine potencies observed for a first set of pre-formulation samples (Sample Nos. 1-8) containing 0.5% w/v lidocaine hydrochloride (HCl) with epinephrine (10.5 mcg/mL), sodium chloride (7 mg/mL), sodium metabisulfite (5.45 mcg/mL), EDTA (0.2 mg/mL or 0.6 mg/mL), about 5 mM of citrate buffer, with a sufficient amount (qs) of sterile water for injection (SWFI) to bring the pre-formulation sample volume to 1 mL.

Table 1b summarizes the compositional makeup and epinephrine potencies observed for a second set of pre-formulation samples (Sample Nos. 9-16) containing 1.0% w/v lidocaine hydrochloride (HCl) with epinephrine (10.5 mcg/mL), sodium chloride (7 mg/mL), sodium metabisulfite (5.45 mcg/mL), EDTA (0.2 mg/mL or 0.6 mg/mL), about 10 mM of citrate buffer, with a sufficient amount (qs) of sterile water for injection (SWFI) to bring the pre-formulation sample volume to 1 mL.

TABLE 1a

Sample Nos. 1-8—0.5% Lidocaine with Epinephrine

| Ingredients/Results | Sample Nos. | | | | | | | |
|---|---|---|---|---|---|---|---|---|
| | 1 | 2 | 3 | 4 | 5 | 6 | 7 | 8 |
| Lidocaine HCl MH,‡ mg/mL | 5.33 | 5.33 | 5.33 | 5.33 | 5.33 | 5.33 | 5.33 | 5.33 |

TABLE 1a-continued

Sample Nos. 1-8—0.5% Lidocaine with Epinephrine

| Ingredients/Results | Sample Nos. | | | | | | | |
|---|---|---|---|---|---|---|---|---|
| | 1 | 2 | 3 | 4 | 5 | 6 | 7 | 8 |
| Epinephrine,† mcg/mL | 10.5 | 10.5 | 10.5 | 10.5 | 10.5 | 10.5 | 10.5 | 10.5 |
| Sodium Chloride, mg/mL | 7 | 7 | 7 | 7 | 7 | 7 | 7 | 7 |
| Sodium Metabisulfite,‡ mcg/mL | 5.45 | 5.45 | 5.45 | 5.45 | 5.45 | 5.45 | 5.45 | 5.45 |
| EDTA Sodium, mg/mL | 0.2 | 0.2 | 0.2 | 0.2 | 0.6 | 0.6 | 0.6 | 0.6 |
| Sodium Citrate DH, mg/mL | 0.876 | 1.013 | 1.155 | 1.225 | 0.876 | 1.013 | 1.155 | 1.225 |
| Citric Acid, mg/mL | 0.286 | 0.1825 | 0.073 | 0.019 | 0.286 | 0.1825 | 0.073 | 0.019 |
| SWFI, qs to 1 mL | qs | qs | qs | qs | qs | qs | qs | qs |
| pHi | 5.552 | 6.042 | 6.497 | 7.068 | 5.558 | 6.074 | 6.512 | 7.069 |
| pHf | 5.151 | 5.714 | 5.967 | 6.228 | 5.064 | 5.597 | 5.863 | 6.071 |
| IP, % | 105.2 | 104.8 | 103.6 | 101.3 | 105.2 | 104.8 | 102.8 | 100.9 |
| DFP | D60 | D60 | D60 | D60 | D60 | D60 | D60 | D60 |
| FP, % | 104.2 | 101.5 | 96.5 | 88 | 104.4 | 100.6 | 97.3 | 91.7 |
| Stability, % | 1% | 3.1% | 6.90% | 13.13% | 0.80% | 4.00% | 5.40% | 9.12% |

Abbreviations/Notes:
MH: Monohydrate;
‡ 5.33 mg/mL of Lidocaine HCl MH corresponds to 5 mg/mL of Lidocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency at 5° C.; FP: Final Potency; Stability, Epinephrine concentration lost from initial concentration (%).

TABLE 1b

Sample Nos. 9-16—1.0% Lidocaine with Epinephrine

| Ingredients/Results | Sample No. | | | | | | | |
|---|---|---|---|---|---|---|---|---|
| | 9 | 10 | 11 | 12 | 13 | 14 | 15 | 16 |
| Lidocaine HCl MH,‡ mg/mL | 10.661 | 10.661 | 10.661 | 10.661 | 10.661 | 10.661 | 10.661 | 10.661 |
| Epinephrine,† mcg/mL | 10.5 | 10.5 | 10.5 | 10.5 | 10.5 | 10.5 | 10.5 | 10.5 |
| Sodium Chloride, mg/mL | 7 | 7 | 7 | 7 | 7 | 7 | 7 | 7 |
| Sodium Metabisulfite,‡ mcg/mL | 5.45 | 5.45 | 5.45 | 5.45 | 5.45 | 5.45 | 5.45 | 5.45 |
| EDTA Sodium, mg/mL | 0.2 | 0.2 | 0.2 | 0.2 | 0.6 | 0.6 | 0.6 | 0.6 |
| Sodium Citrate DH, mg/mL | 1.751 | 2.026 | 2.31 | 2.45 | 1.751 | 2.026 | 2.31 | 2.45 |
| Citric Acid, mg/mL | 0.572 | 0.365 | 0.146 | 0.038 | 0.572 | 0.365 | 0.146 | 0.038 |
| SWFI, qs to 1 mL | qs | qs | qs | qs | qs | qs | qs | qs |
| pHi | 5.552 | 6.042 | 6.497 | 7.068 | 5.558 | 6.074 | 6.512 | 7.069 |
| pHf | 5.17 | 5.676 | 5.989 | 6.3 | 5.192 | 5.611 | 5.908 | 6.165 |
| IP, % | 105.4 | 103.3 | 102.8 | 98.9 | 105.2 | 102.7 | 102.7 | 99.7 |
| DFP | D60 | D60 | D60 | D15 | D60 | D60 | D60 | D15/D28 |
| FP, % | 103.4 | 97 | 85.1 | 89.5 | 103.3 | 97.2 | 88.7 | 92.4/88.1 |
| Stability, % | 1.90% | 6.10% | 17.22% | 9.50% | 1.81% | 5.36% | 13.63% | 7.3%/11.65% |

Abbreviations/Notes:
MH: Monohydrate;
‡ 10.661 mg/mL of Lidocaine HCl MH corresponds to 10 mg/mL of Lidocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency at 5° C.; FP: Final Potency; Stability, Epinephrine concentration lost from initial concentration (%).

Based on the results of the first study, the following observations were made.

Consistent with known results (see e.g., Larson), epinephrine degrades to a greater degree with increasing pH. For instance, the epinephrine potency for Sample No. 1 (pH≈5.5) after 60-days of storage at about 5° C. was observed to be about 104%, while the epinephrine potency for Sample No. 4 (pH≈7.0) after 60-days of storage at about 5° C. was observed to be about 88%.

Epinephrine degradation is promoted by an increase in citrate buffer concentration. For instance, the epinephrine potency for Sample No. 8 (pH≈7.0, citrate≈5 mM) after 60-days of storage at about 5° C. was observed to be about 92%, while the epinephrine potency for Sample No. 16

(pH≈7.0, citrate≈10 mM) after 28-days of storage at about 5° C. was observed to be about 88%.

Epinephrine degradation is retarded by an increase in EDTA concentration. For instance, the epinephrine potency for Sample No. 8 (pH≈7.0, EDTA≈0.6 mg/mL) after 60-days of storage at about 5° C. was observed to be about 92%, while the epinephrine potency for Sample No. 4 (pH≈7.0, EDTA≈0.2 mg/mL) after 28-days of storage at about 5° C. was observed to be about 88%.

A second study of epinephrine potency occurred for six preformulation samples (viz., Sample Nos. 17-22) containing 1.0% w/v lidocaine HCl with epinephrine without any sodium metabisulfite each at a constant pH of about 6.5. The second study evaluated epinephrine potency at a citrate buffer concentration of about 20 mM (Sample Nos. 17-19) with (a) no EDTA (Sample No. 17), (b) EDTA (Sample No. 18), and (c) EDTA and ascorbic acid (Sample No. 19). The second study also evaluated epinephrine potency at a phosphate buffer concentration of about 10 mM (Sample Nos. 20-21) with (a) no EDTA (Sample No. 20), (b) EDTA (Sample No. 21), and (c) EDTA and ascorbic acid (Sample No. 22).

Samples were prepared as described herein and stored under refrigerated conditions (about 5° C.) and protected from light. Lidocaine and epinephrine potencies were evaluated by UPLC. Table 2 summarizes the compositional details and results of the second study.

degradation is similar for both citrate (≈20 mM) buffer and phosphate (≈10 mM) buffer. Additionally, the results of the second study suggest that epinephrine degrades to a greater degree either in the presence of EDTA (cf. Sample No. 17 and Sample No. 18) or in the presence of EDTA and ascorbic acid (cf. Sample No. 17 and Sample No. 19).

As stated above, Edge Pharma's lidocaine with epinephrine having a BUD of 30-days utilizes phosphate buffer. Based on the results mentioned herein, phosphate shows long-term incompatibility with respect to epinephrine degradation. Not to be limited by data interpretation, the problem with a phosphate buffer relates to oxidative potentiation of epinephrine.

A third study of epinephrine potency occurred for ten preformulation samples (viz., Sample Nos. 23-32) containing 1.0% w/v lidocaine HCl with epinephrine each containing sodium metabisulfite (≈5.5 mcg/mL) and each having a pH of about 6.5 or about 6.7. The third study evaluated epinephrine potency at a citrate buffer concentration of about 20 mM (Sample Nos. 23-25) with (a) no EDTA (Sample No. 23), (b) EDTA and ascorbic acid (Sample No. 24), and (c) EDTA and L-cysteine (Sample No. 25). The third study also evaluated epinephrine potency at a phosphate buffer concentration of about 10 mM (Sample Nos. 26-28) with (a) no EDTA (Sample No. 26), (b) EDTA and ascorbic acid (Sample No. 27), and (c) EDTA and L-cysteine (Sample No. 28). The third study further evaluated epineph-

TABLE 2

Sample Nos. 17-22—1.0% Lidocaine with Epinephrine with no SMB

| Ingredients/Results | Sample Nos. | | | | | |
| --- | --- | --- | --- | --- | --- | --- |
| | 17 | 18 | 19 | 20 | 21 | 22 |
| Lidocaine HCl MH,‡ mg/mL | 10.661 | 10.661 | 10.661 | 10.661 | 10.661 | 10.661 |
| Epinephrine, mcg/mL | 10 | 10 | 10 | 10 | 10 | 10 |
| NaCl, mg/mL | 7 | 7 | 7 | 7 | 7 | 7 |
| EDTA Sodium, mg/mL | — | 0.2 | 0.2 | — | 0.2 | 0.2 |
| Sodium Citrate DH, mg/mL | 4.26 | 4.26 | 4.26 | — | — | — |
| Citric Acid, mg/mL | 0.292 | 0.292 | 0.292 | 0.262 | 0.262 | 0.262 |
| Disodium Phosphate, mg/mL | — | — | — | 41.03 | 41.03 | 41.03 |
| Ascorbic Acid, mg/mL | — | — | 0.2 | — | — | 0.2 |
| SWFI, qs to 1 mL | qs | qs | qs | qs | qs | qs |
| pHi | 6.509 | 6.451 | 6.471 | 6.471 | 6.451 | 6.506 |
| pHf | 6.516 | 6.421 | 6.464 | 6.481 | 6.423 | 6.471 |
| IP, % | 92.8 | 84.8 | 66.5 | 91.0 | 84.1 | 62.0 |
| DFP | D12 | D12 | D12 | D12 | D12 | D12 |
| FP, % | 88.4 | 78.8 | 59.5 | 87.4 | 79.1 | 53.0 |
| Stability, % | 4.74% | 7.08% | 10.53% | 3.96% | 5.95% | 14.52% |

Abbreviations/Notes:
MH: Monohydrate;
‡10.661 mg/mL of Lidocaine HCl MH corresponds to 10 mg/mL of Lidocaine HCl;
DH; Dihydrate; SWFI: Sterile Water for Injection; pHi: initial pH; pHf: final pH; IP: Initial Potency; DFP: Day for final Potency at 5° C.; FP: Final Potency; Stability, Epinephrine concentration lost from initial concentration (%).

Based on the results of the second study, the following observations were made.

Epinephrine potencies after 12-days of storage at about 5° C. were low. Data (not shown) reveals that epinephrine degradation proceeds for about 8 days and then slows thereafter.

Consistent with the results of the first study, the results of the second study show that epinephrine degradation occurs rapidly with increased citrate buffer concentration. Interestingly, the results of the second study shows that epinephrine rine potency at a citrate buffer concentration of about 10 mM (Sample Nos. 26-28) with differing amounts of EDTA (viz., 1.2 mg/mL (Sample Nos. 29-30) and 2 mg/mL (Sample Nos. 31-32).

Samples were prepared as described herein and stored under refrigerated conditions (about 5° C.) and protected from light. Lidocaine and epinephrine potencies were evaluated by UPLC. Table 3 summarizes the compositional details and results of the third study.

TABLE 3

Sample Nos. 23-32—1.0% Lidocaine with Epinephrine with SMB

| Ingredients/Results | Sample Nos. | | | | | | | | | |
|---|---|---|---|---|---|---|---|---|---|---|
| | 23 | 24 | 25 | 26 | 27 | 28 | 29 | 30 | 31 | 32 |
| Lidocaine HCl MH,‡ mg/mL | 10.661 | 10.661 | 10.661 | 10.661 | 10.661 | 10.661 | 10.661 | 10.661 | 10.661 | 10.661 |
| Epinephrine,† mcg/mL | 10.5 | 10.5 | 10.5 | 10.5 | 10.5 | 10.5 | 10.5 | 10.5 | 10.5 | 10.5 |
| NaCl, mg/mL | 7 | 7 | 7 | 7 | 7 | 7 | 7 | 7 | 7 | 7 |
| SMB,‡ mcg/mL | 5.45 | 5.45 | 5.45 | 5.45 | 5.45 | 5.45 | 5.45 | 5.45 | 5.45 | 5.45 |
| EDTA Sodium, mg/mL | — | 0.2 | 0.2 | — | 0.2 | 0.2 | 1.2 | 1.2 | 2 | 2 |
| Sodium Citrate DH, mg/mL | 4.26 | 4.26 | 4.26 | — | — | — | 2.31 | 2.38 | 2.31 | 2.38 |
| Citric Acid, mg/mL | 0.292 | 0.292 | 0.292 | 0.262 | 0.262 | 0.262 | 0.146 | 0.092 | 0.146 | 0.092 |
| Disodium Phosphate, mg/mL | — | — | — | 41.03 | 41.03 | 41.03 | — | — | — | — |
| Ascorbic Acid, mg | — | 1 | — | — | 1 | — | — | — | — | — |
| L-Cys, mg/mL | — | — | 1 | — | — | 1 | — | — | — | — |
| SWFI, qs to 1 mL | qs | qs | qs | qs | qs | qs | qs | qs | qs | qs |
| pHi | 6.557 | 6.512 | 6.524 | 6.523 | 6.521 | 6.595 | 6.574 | 6.764 | 6.529 | 6.771 |
| pHf | 6.574 | 6.52 | 6.503 | 6.543 | 6.544 | 6.581 | 6.539 | 6.789 | 6.546 | 6.78 |
| IP,% | 101.8 | 54.8 | 82.8 | 98.4 | 50.2 | 75.9 | 81.7 | 67.8 | 82.7 | 63.5 |
| DFP | D19 | D19 | D19 | D19 | D19 | D19 | D19 | D19 | D19 | D19 |
| FP, % | 91.2 | 69.8 | 74.1 | 88.9 | 64.9 | 82.2 | 57.0 | 40.0 | 60.8 | 61.5 |
| Stability, % | 10.41 | 27.37 | 10.51 | 9.65 | 29.28 | 8.30 | 30.23 | 41.00 | 26.48 | 3.15 |

Abbreviations/Notes:
MH: Monohydrate;
‡ 10.661 mg/mL of Lidocaine HCl MH corresponds to 10 mg/mL of Lindocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency; Stability, Epinephrine concentration lost from inital from initial concentration (%).

Based on the results of the third study, the following observations were made.

Epinephrine potencies after 19-days of storage at about 5° C. were low. Epinephrine is not stable in the samples with SMB, SMB and ascorbic acid, or SMB and NAC at pH of about 6.5 or a pH of about 6.7.

A fourth study of epinephrine potency occurred for eight pre-formulation samples (viz., Sample Nos. 33-40) containing 1.0% w/v lidocaine HCl with epinephrine having a reduced amount (≈4.8-4.9 mM) of citrate buffer.

The fourth study evaluated epinephrine potency with respect to different EDTA concentrations, pH, formaldehyde-sodium bisulfite adduct (viz., FSB; CAS No. 870-72-4), and N-acetyl-L-cysteine (viz., NAC).

Samples were prepared as described herein and stored under refrigerated conditions (about 5° C.) and protected from light. Lidocaine and epinephrine potencies were evaluated by UPLC. Table 4 summarizes the compositional details and results of the fourth study.

TABLE 4

Sample Nos. 33-40—1.0% Lidocaine with Epinephrine

| Ingredients/Results | Sample Nos. | | | | | | | |
|---|---|---|---|---|---|---|---|---|
| | 33 | 34 | 35 | 36 | 37 | 38 | 39 | 40 |
| Lidocaine HCl MH,‡ mg/mL | 10.66 | 10.66 | 10.66 | 10.66 | 10.66 | 10.66 | 10.66 | 10.66 |
| Epinephrine,† mcg/mL | 10.5 | 10.5 | 10.5 | 10.5 | 10.5 | 10.5 | 10.5 | 10.5 |
| NaCl, mg/mL | 7 | 7 | 7 | 7 | 7 | 7 | 7 | 7 |
| SMB,‡ mcg/mL | 5.17 | 5.17 | 5.17 | 5.17 | 5.17 | 5.17 | — | — |
| EDTA Sodium, mg/mL | 0.2 | 0.2 | 0.6 | 0.6 | 0.2 | 0.6 | — | — |

TABLE 4-continued

Sample Nos. 33-40—1.0% Lidocaine with Epinephrine

| Ingredients/ Results | Sample Nos. | | | | | | | |
|---|---|---|---|---|---|---|---|---|
| | 33 | 34 | 35 | 36 | 37 | 38 | 39 | 40 |
| Sodium Citrate DH, mg/mL | 1.155 | 1.225 | 1.155 | 1.225 | 1.225 | 1.225 | 1.225 | 1.225 |
| Citric Acid, mg/mL | 0.073 | 0.019 | 0.073 | 0.019 | 0.019 | 0.019 | 0.019 | 0.019 |
| FSB, mg/mL | — | — | — | — | 0.1 | 0.1 | — | — |
| NAC, mcg/mL | — | — | — | — | — | — | 10.5 | 50 |
| SWFI, qs to 1 mL | 1 | 1 | 1 | 1 | 1 | 1 | 1 | 1 |
| pHi | 6.564 | 7.012 | 6.584 | 7.014 | 7.022 | 7.072 | 7.022 | 7.012 |
| pHf | 6.542 | 6.986 | 6.550 | 6.993 | 7.002 | 7.057 | 6.990 | 6.979 |
| IP, % | 103.1 | 100.8 | 102.2 | 100.7 | 92.6 | 92.9 | 106.5 | 105 |
| DFP | D7 | D7 | D7 | D7 | D7 | D7 | D7/D18 | D7/18 |
| FP, % | 87 | 83 | 86.7 | 81.1 | 45.6 | 43 | 104.2/85 | 98.8/87.4 |
| Stability, % | 15.62% | 17.66% | 15.17% | 19.46% | 50.76% | 53.71% | 2.2%/ 20% | 5.9%/ 16.8% |

Abbreviations/Notes:
MH: Monohydrate;
‡ 10.661 mg/mL of Lidocaine HCl MH corresponds to 10 mg/mL of Lindocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency; Stability, Epinephrine concentration lost from inital from initial concentration (%)

The results of the fourth study show that N-acetyl-L-cysteine (NAC) tends to retard epinephrine degradation.

A fifth study of epinephrine potency occurred for four pre-formulation samples (viz., Sample Nos. 41-44) containing 0.5% w/v lidocaine HCl with epinephrine with the aim of evaluating which single antioxidant (viz., SVB or NAC) retarded epinephrine degradation.

Samples were prepared as described herein and stored under refrigerated conditions (about 5° C.) and protected from light. Lidocaine and epinephrine potencies were evaluated by UPLC. Table 5 summarizes the compositional details and results of the fifth study.

TABLE 5

Sample Nos. 41-44—0.5% Lidocaine with Epinephrine

| Ingredients/Results | Sample Nos. | | | |
|---|---|---|---|---|
| | 41 | 42 | 43 | 44 |
| Lido HCL MH,‡ mg/mL | 5.33 | 5.33 | 5.33 | 5.33 |
| Epi, mcg/mL | 10.5 | 10.5 | 10.5 | 10.5 |
| NaCl, mg/mL | 7 | 7 | 7 | 7 |
| SMB, mcg/mL | 5.17 | — | — | — |
| EDTA Sodium, mg/mL | 0.6 | — | — | — |
| SC DH, mg/mL | 1.225 | 1.225 | 1.155 | 1.013 |
| CA, mg/mL | 0.019 | 0.019 | 0.073 | 0.1825 |
| NAC, mcg/mL | — | 10.5 | 10.5 | 10.5 |
| SWFI, qs to 1 mL | qs | qs | qs | qs |
| pHi | 7.078 | 7.046 | 6.659 | 6.057 |
| pHi | 7.111 | 7.093 | 6.664 | 6.029 |
| IP, % | 97.5 | 103.9 | 106 | 106.6 |

TABLE 5-continued

Sample Nos. 41-44—0.5% Lidocaine with Epinephrine

| Ingredients/Results | Sample Nos. | | | |
|---|---|---|---|---|
| | 41 | 42 | 43 | 44 |
| DFP | D23 | D27 | D23 | D27 |
| FP, % | 74.0 | 92.2 | 85.0 | 96.9 |
| Stability, % | 24.10% | 11.26% | 19.81% | 9.10% |

Abbreviations/Notes:
MH: Monohydrate;
‡ 5.33 mg/mL of Lidocaine HCl MH corresponds to 5 mg/mL of Lidocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency at 5° C.; FP: Final Potency; Stability, Epinephrine concentration lost from initial concentration (%).

The results from the fifth study shows that epinephrine degradation occurs to a greater degree in the presence of SMB (cf. Sample No. 41) compared to NAC (cf. Sample No. 42). The results also show that epinephrine degradation occurs to a lesser degree with reduced pH (cf. Samples No. 42 and 44) with a constant amount of NAC. It is believed that the observed increase of epinephrine potency for Sample No. 43 is an aberration.

A sixth study of epinephrine potency occurred for eight pre-formulation samples (viz., Sample Nos. 45-52) containing 0.5% w/v lidocaine HCl with epinephrine with the aim of evaluating a combination of SMB, NAC, and pH that provides a suitable epinephrine potency.

Samples were prepared as described herein and stored under refrigerated conditions (about 5° C.) and protected from light. Lidocaine and epinephrine potencies were evaluated by UPLC. Table 5 summarizes the compositional details and results of the fifth study.

TABLE 6

Sample Nos. 45-52—0.5% Lidocaine with Epinephrine with SMB or SMB and NAC

| Ingredients/ Results | Sample Nos. | | | | | | | |
|---|---|---|---|---|---|---|---|---|
| | 45 | 46 | 47 | 48 | 49 | 50 | 51 | 52 |
| Lido HCL MH,‡ mg/mL | 5.33 | 5.33 | 5.33 | 5.33 | 5.33 | 5.33 | 5.33 | 5.33 |
| Epi,† mcg/mL | 10.5 | 10.5 | 10.5 | 10.5 | 10.5 | 10.5 | 10.5 | 10.5 |
| NaCl, mg/mL | 7 | 7 | 7 | 7 | 7 | 7 | 7 | 7 |
| SMB,‡ mcg/mL | 5.45 | 5.17 | 5.17 | 5.17 | 5.17 | 5.17 | 5.17 | 5.17 |
| EDTA Sodium, mg/mL | 0.6 | 0.6 | 0.6 | 0.6 | 0.6 | 0.6 | 0.6 | 0.6 |
| SC DH, mg/mL | 0.876 | 1.013 | 1.155 | 1.225 | 1.013 | 1.013 | 1.013 | 1.225 |
| CA, mg/mL | 0.286 | 0.1825 | 0.073 | 0.019 | 0.1825 | 0.1825 | 0.1825 | 0.019 |
| NAC, mcg/mL | — | — | — | — | 10.5 | — | 10.5 | — |
| SWFI, qs to 1 mL | qs | qs | qs | qs | qs | qs | qs | qs |
| pHi | 6.44 | 6.505 | 6.488 | 6.473 | 6.393 | 6.166 | 6.138 | 6.136 |
| IP, % | 97.8 | 101.9 | 103.6 | 101.4 | 102.8 | 102.9 | 102.7 | 104.4 |
| PD60, % | 31.7 | 88.4 | 88.8 | 72.8 | 95.0 | 97.1 | 96.5 | 87.6 |
| pH, D60 | — | — | — | — | 6.395 | 6.158 | 6.110 | — |
| PD75, % | 21.8 | 82.8 | 82.4 | 62.3 | 92.3 | 93.7 | 94.2 | 81.3 |
| pH, D75 | — | — | — | — | 6.390 | 6.136 | 6.105 | — |
| PD90, % | 15.0 | 783. | 77.5 | 50.0 | 90.0 | 92.2 | 92.7 | 76.0 |
| pH, D90 | — | — | — | — | 6.441 | 6.217 | 6.194 | — |

Abbreviations/Notes:
MH: Monohydrate;
‡ 5.33 mg/mL of Lidocaine HCl MH corresponds to 5 mg/mL of Lidocaine HCl;
† 5% overage;
‡ Based on 5% epinephrine overage.
DH; Dihydrate; SWFI: Sterile Water for Injection; pHi: initial pH; pHf: final pH; IP: Initial Potency; DFP: Day for final Potency at 5° C.; FP: Final Potency; Stability, Epinephrine concentration lost from initial concentration (%).

The results from the sixth study shows that epinephrine degradation occurs to a lesser degree for Samples Nos. 49-51.

Example 1-0.5% Lidocaine with Epinephrine (3 L Batch)

The table that follows summarizes the compositional makeup of a batch volume of about 3, 100 mL, where the epinephrine overage may be about 5% over the labeled content of 10 mcg/mL

| Ingredients | Concentration |
|---|---|
| Lidocaine HCl Monohydrate‡ | 5.33 mg/mL |
| Epinephrine | 10.5 mcg/mL |
| Sodium Chloride | 7 mg/mL |
| Sodium Metabisulfite | 5.45 mcg/mL |
| EDTA Sodium,† | 0.6 mg/mL |
| Sodium Citrate Dihydrate‡ | 1.013 mg/mL |
| Citrate Acid | 0.1825 mg/mL |
| N-Acetyl-L-Cysteine | 13 mcg/mL |
| pH Adjuster∦ | qs |
| SWFI, qs to 3100 mL | qs |

Notes:
‡ 5.33 mg/mL of Lidocaine HCl Monohydrate corresponds to 5.0 mg/mL Lidocaine HCl.
† Concentration of EDTA (free acid) is 0.47 mg/mL.
‡ Concentration of Sodium Citrate is 0.889 mg/mL.
∦ 10% HCl and/or 10% NaOH qs. to target pH of about 6.4 (pH range of about 6.3 to 6.5).

The 3 L Batch of 0.5% Lidocaine with Epinephrine (Ex. 1) was prepared as follows.
1. Wrap a 5 L container ("C1") with amber bag for light protection. Add 2000 mL SWFI to C1.
2. Add the following powders to the SWFI in C1 under stirring and mix to dissolve: Sodium Citrate 3.14 g±2% (3.08-3.20 g); Citrate Acid 565.8 mg±2% (554.4-577.1 mg); Sodium Chloride 21.7 g±2% (21.27 g-22.13 g); Lidocaine HCL (monohydrate) 16.52 g±2% (16.19 g-16.85 g);
3. Mix the contents of C1 for a minimum of 30-minutes with the aim of obtaining complete dissolution. The contents of C1 with be mixed with Epinephrine sub solution in step 5.
4. Epinephrine/Antioxidant solution (about 800 mL)
  4.1. Sodium Metabisulfite (SMB) Solution (about 150 mL of about 0.338 mg/mL)
    a. Add 120 mL SWFI to a container ("C2," e.g., 200 mL bottle).
    b. Add Sodium Metabisulfite (SMB) 50.7 mg (50.7-51.71 mg) into C2.
    c. Cap C2 and stir 15 minutes to dissolve the SMB powder completely.
    d. QS to 150 mL with SWFI and mix for 5 minutes.
  4.2. N-Acetyl-L-Cysteine (NAC) Solution (about 10 mL)
    a. Add about 10 mL SWFI to a container ("C3," e.g., 20 mL bottle).
    b. Add N-Acetyl-L-Cysteine 40.30 mg (40.30 mg-41.11 mg).
    c. Cap C3 and stir 5-10 minutes to dissolve the NAC powder completely.
  4.3. Epinephrine/EDTA Solution (about 700 mL)
    a. Wrap a 1 L container ("C4") and add 500 mL SWFI.
    b. Add EDTA disodium dihydrate 1.86 g±2% (1.82 g-1.70 g) to C4 under stirring and stir to dissolve the powder.
    c. Adjust pH to 2.6-2.7 (record target pH).
    d. Add Epinephrine 32.55 mg+2% (32.55 mg-33.20 mg) to C4 while stirring. Rinse weighing bowl (×3) adding contents to C4.
    e. Make up to 700 mL with SWFI.
    f. Cap the bottle and stir to dissolve Epinephrine powder for 30 minutes.

g. Check pH and ensure the pH is below 3.0. (If pH is >3.0, repeat step c to e).

h. Continue immediately to step 4.4.

EDTA Sodium form converts slowly to EDTA acid at low pH and may precipitate. The solution may become hazy after 50 minutes at pH 2.55-2.65. The precipitates will be re-dissolved automatically in step 5.

4.4. Preparing Epi/SMB/NAC Mixture Solution a. Measure exactly 50 mL of SMB Solution from C2 and add to C4 with continued stirring.

b. Add contents of C3 (NAC Solution, from step 4.2) into C4 with continued stirring.

c. Rinse C2 (SMB Solution) and C3 (NAC Solution) with SWFI (×3) adding rinses to C4 with stirring. Total Mixture Solution volume is about 800 mL.

d. Continue immediately to step 5.

5. Add all the contents of C4 (from step 4.4.c, i.e., Epi/SMB/NAC/EDTA Solution) into C1 under stirring. Rinse C4 with SWFI and add it into C1. Mix C1 contents for 10-15 mins.

6. Adjust pH to 6.4 (acceptable range of 6.3-6.4) using 10% HCl and/or 10% NaOH. The solution should be completely clear.

7. QS to 3100 mL with SWFI and mix for 5 minutes.

8. Transfer 3100 mL into 3 L bag. Filling and Weighing 3 L Bulk Bags for Transfer. Record bag weight.

9. Document Filtration and Filling Date.

10. Filter the solution using a polyethersulfone ("PES") filter (0.22 μm).

11. Fill 5 mL of solution in each 5 mL BD syringe and fit syringe with Luer-Lok tip.

12. Record the number of filled syringes.

Samples were stored under refrigerated conditions (about 5° C.) and protected from light. Lidocaine and epinephrine potencies were evaluated by UPLC. Table 7 summarizes selected parameters of the Example 1 formulation.

| Ingredients | Concn. |
|---|---|
| Lidocaine HCl Monohydrate‡ | 10.66 mg/mL |
| Epinephrine | 10.5 mcg/mL |
| Sodium Chloride | 6 mg/mL |
| Sodium Metabisulfite | 5.45 mcg/mL |
| EDTA Sodium† | 0.6 mg/mL |
| Sodium Citrate Dihydrate‡ | 1.013 mg/mL |
| Citrate Acid | 0.1825 mg/mL |
| N-Acetyl-L-Cysteine | 13 mcg/mL |
| 10% HCl and/or 10% NaOH qs. to target pH of about 6.34§ | qs to pH 6.34 |
| SWFi, qs to 9300 mL | qs |

Notes:

‡ 10.66 mg/mL of Lidocaine HCl Monohydrate corresponds to 10 mg/mL Lidocaine HCl.

† Concentration of EDTA (free acid) is 0.47 mg/mL.

‡ Concentration of Sodium Citrate is 0.889 mg/mL.

§ 10% HCl and/or 10% NaOH qs. to target pH of about 6.34 (pH range of about 6.3 to about 6.4).

The 9 L Batch of 1.0% Lidocaine with Epinephrine (Ex. 2) was prepared as follows.

1. Record start time and date.

2. Sodium Metabisulfite sub formulation of concentration about 0.338 mg/mL (about 350 mL):

a. Add about 280 mL of SWFI in a 500 mL beaker, and dissolve sodium metabisulfite while stirring.

b. Rinse the weighing boat and QS to about 350 mL (Final volume) and stir for minimum of 5 minutes.

3. Lidocaine sub-formulation (about 6,000 mL)—protect a 18 L jug from light throughout the compounding process.

4. In about 4,800 mL (80% of total volume) SWFI, add and dissolve while stirring the following ingredients:

Sodium citrate dihydrate (9.4209 g±2%, Range 9.2325 g-9.6093 g);

Citric acid anhydrous (1.6973 g±2%, Range 1.6633 g-1.7312 g);

Sodium chloride granular (55.8 g±2%, Range 54.684 g-56.916 g); and

TABLE 7

| | 0.5% Lidocaine with Epinephrine | | | | | | | |
|---|---|---|---|---|---|---|---|---|
| | Day | | | | | | | |
| | 0 | 30 | 45 | 60 | 75 | 90 | Δ60,$^a$% | Δ90,$^b$% |
| Lidocaine† | 100.9% | 99.3% | 99.9% | 99.1% | 99.8% | 99.4% | 1.8% | 1.5% |
| Epinephrine‡ | 100.3% | 96.8% | 95.1% | 94.4% | 93.8% | 92.5% | 5.9% | 7.8% |
| Sterility <71>‡ | Negative | Negative | — | Negative | — | — | N/A | N/A |
| Particulate Matter§ | Conforms | — | — | — | — | Conforms | N/A | N/A |
| pH | 6.3 | 6.41 | — | 6.40 | — | 6.33 | — | — |

$^a$Δ60 is the potency at day 0 less the potency at day 60.

$^b$Δ90 is the potency at day 0 less the potency at day 90.

† Acceptable lidocaine potency limit of 90% to 110%.

‡ Acceptable epinephrine potency limit of 90% to 115%.

‡ Sterility per USP <71> after 14 day incubation.

§ Particulate matter ("PM") ≥ 10 μm is ≤ 6000/container, while PM ≥ 25 μm is ≤ 600/container.

Potency testing shows that the ready-to-use formulation has a stability such that each of lidocaine and epinephrine has a potency of at least 90% after storage for about 90-days at a temperature of about 5° C.

Example 2-1.0% Lidocaine with Epinephrine (9 L Batch)

The table that follows summarizes the compositional makeup of a batch volume of about 9,300 mL, where the epinephrine overage may be about 5% over the labeled content of 10 mcg/mL.

Lidocaine HCl monohydrate (99.138 g±2%, Range 97.158 g-101.118 g).

5. Stir for minimum of 30 minutes and until all ingredients are dissolved completely; record stirring start and stop times.

6. QS to 6,000 mL (Final volume) using SWFI

7. Epinephrine sub formulation (about 2,400 mL). Note: This sub formulation may be started while Lidocaine sub-formulation is stirring. Protect a 3 L beaker from light throughout the compounding process.

8. In 1,500 mL of SWFI (approximately 62% of total volume), add and dissolve EDTA disodium dihydrate (5.58 g±2%, Range 5.4684 g-5.6916 g).

9. Stir for minimum of 15 minutes and until dissolved. Record stirring start and stop times.

10. Record initial pH, and, if necessary, adjust pH to 2.65 (acceptable pH range of 2.6-2.7) using 10% HCl and/or 10% NaOH.

11. Add Epinephrine base (0.09765 g+2%, Range 0.09765 g-0.09960 g) and stir until dissolved.

12. Stir until dissolved; record stirring start and stop times.

13. Check pH. Target pH: 2.65 (pH should fall between 2.6-2.7.
   a. If no pH adjustment necessary, then proceed to step 14.
   b. If pH adjustment necessary, then adjust pH to 2.65 (range 2.6-2.7) using 10% HCl and/or 10% NaOH.

Cloudiness may be observed in the sub-formulation with no impact.

14. Measure and add about 150 mL of sodium metabisulfite solution in the beaker.

15. Add N-Acetyl-L-Cysteine 0.1209 g (range, 0.1209 g-0.1233 g), in the solution. Stir for 5 minutes.

16. QS to about 2,400 mL (Final volume) using SWFI and stir for minimum of 5 minutes.

17. Add Epinephrine sub-formulation into Lidocaine HCl sub-formulation.

18. Stir for minimum of 15 minutes; record stirring start and stop times.

19. Measure and record pH. If necessary, adjust pH to 6.34 (Range: 6.29-6.38) using 10% HCl and/or 10% NaOH. Solution should be clear at this step.

20. QS to about 9,300 mL (Final volume) using SWFI and stir for 5 minutes.

21. Obtain unfiltered samples from Top and Bottom directly from jug.

22. Transfer 3,100 mL of solution into each empty ethylene vinyl acetate ("EVA") bag(s).

23. Continue filling bag until obtaining an approximate target weight between 3093 g-3243 g.

24. Document Filtration and Filling Date.

25. Filter the solution using a polyethersulfone ("PES") filter (0.22 μm).

26. Fill 5 mL of solution in each 5 mL BD syringe and fit syringe with Luer-Lok tip.

27. Record the number of filled syringes.

Filled syringes were stored under refrigerated conditions (about 5° C.) and protected from light. Lidocaine and epinephrine potencies were evaluated by UPLC.

Example 3—1.0% Lidocaine with Epinephrine (9 L Batch, 8% Epinephrine Overage)

The table that follows summarizes the compositional makeup of a batch volume of about 9,300 mL, where the epinephrine overage is about 8% over the labeled content of 10 mcg/mL.

| Ingredients | Concn. |
|---|---|
| Lidocaine HCl | 10 mg/mL |
| Epinephrine | 10.8 mcg/mL |
| Sodium Chloride | 6 mg/mL |
| Sodium Metabisulfite | 5.6 mcg/mL |
| EDTA Sodium† | 0.6 mg/mL |
| Sodium Citrate‡ | 1.013 mg/mL |
| Citric Acid | 0.1825 mg/mL |
| N-Acetyl-L-Cysteine | 13 mcg/mL |
| 10% HCl and/or 10% NaOH qs. to target pH of about 6.34 | qs to pH 6.34 |
| SWFi, qs to 9300 mL | qs |

Notes:
‡ 10.66 mg/mL of Lidocaine HCl Monohydrate corresponds to 10 mg/mL Lidocaine HCl.
† Concentration of EDTA (free acid) is 0.47 mg/mL.
‡Concentration of Sodium Citrate is 0.889 mg/mL.
§10% HCl and/or 10% NaOH qs. to target pH of about 6.34 (pH range of about 6.3 to about 6.4).

Examples 4-9—Lidocaine with Epinephrine

The table that follows summarizes the compositional makeup of ready-to-use formulations having a variable batch volume, where the epinephrine overage may be about 5% to about 8% over the labeled content of 10 mcg/mL.

| Ingredients | Ex. 4 | Ex. 5 | Ex. 6 | Ex. 7 | Ex. 8 | Ex. 9 |
|---|---|---|---|---|---|---|
| Lidocaine HCl, mg/mL | 5 | 10 | 20 | 5 | 10 | 20 |
| Epinephrine, mcg/mL‡ | 10-10.8 | 10-10.8 | 10-10.8 | 10-10.8 | 10-10.8 | 10-10.8 |
| Sodium Chloride, mg/mL | 6-7 | 6-7 | 6-7 | 6-7 | 6-7 | 6-7 |
| Sodium Metabisulfite,† mcg/mL | 5-5.6 | 5-5.6 | 5-5.6 | 5-5.6 | 5-5.6 | 5-5.6 |
| EDTA Sodium, mg/mL | 0.6 | 0.6 | 0.6 | 0.6 | 0.6 | 0.6 |
| Citrate Buffer, mM | 1-10 | 1-10 | 1-10 | 1-10 | 1-10 | 1-10 |
| N-Acetyl-L-Cysteine,† mcg/mL | 10-13 | 10-13 | 10-13 | — | — | — |
| pH adjuster‡ | qs | qs | qs | qs | qs | qs |
| SWFi, qs to 1 mL | qs | qs | qs | qs | qs | qs |

| Ingredients | Ex. 4 | Ex. 5 | Ex. 6 | Ex. 7 | Ex. 8 | Ex. 9 |
|---|---|---|---|---|---|---|
| Unit Volume, mL | 0.3-55 | 0.3-55 | 0.3-55 | 0.3-55 | 0.3-55 | 0.3-55 |
| Syringe, mL ‡ | 1-60 | 1-60 | 1-60 | 1-60 | 1-60 | 1-60 |

‡ Epinephrine concentration increases with increasing batch size.

† Sodium metabisulfite ("SMB") concentration increases based on the amount of epinephrine, where the mole amount of SMB is about one-half the mole amount of epinephrine.

‡ 10% HCl and/or 10% NaOH qs. to target pH of about 6.4 (pH range of about 6.3 to about 6.5).

‡ The syringes may be fitted with a Luer-Lok tip and have volumes (in mL) of: 1,3,5, 10, 20, 30, and 60.

The ready-to-use liquid formulations exhibit an epinephrine stability that is substantially improved compared to the previous pH-adjusted lidocaine with epinephrine preparations. See e.g., Christoph, Stewart, and Larson. The added stability is particularly surprising since no efforts were made to exclude oxygen and since epinephrine is known to degrade in the presence of oxygen. See e.g., Connors at 440. With the understanding that the ready-to-use liquid formulations may further comprise up to 40 mg/L of oxygen, the stabilities observed herein are especially surprising since the molar ratio of oxygen to epinephrine is about 25 and the molar ratio of oxygen to epinephrine to anti-oxidant (e.g., sodium metabisulfite and/or N-acetyl-L-cysteine) is about 15 to about 48. Further, the ready-to-use liquid formulations exhibit an epinephrine stability that is about two to about three times more stable than the Edge Pharma preparation. Finally, the ready-to-use liquid formulations are substantially more stable than the Xylocaine MPF with Epinephrine product when stored in a syringe protected from light. For instance, experiments show that the Xylocaine MPF with Epinephrine product has less than 90% of the epinephrine content after 24 days when stored at room temperature in a syringe protected from light.

CITED INFORMATION

The following cited information is incorporated by reference in its entirety.

Bernards et al., *Effect of Epinephrine on Lidocaine Clearance In Vivo*, Anesthesiology (1999) 91(4): 962-968 ("Bernards").

Bonhomme et al., *Chemical Stability of Lignocaine (Lidocaine) and Adrenalin (Epinephrine) in pH-adjusted Parenteral Solutions*, J. Clin. Pharm. Thera. (1988) 13(4): 257-261 ("Bonhomme").

Christoph et al., *Pain Reduction in Local Anesthetic Administration through pH Buffering*, Ann. Emerg. Med. (1988) 17(2): 117-120 ("Christoph").

Connors et al., Chemical Stability of Pharmaceuticals: A Handbook for Pharmacists, $2^{nd}$ Ed. (1986), pp. 438-448 ("Connors").

Edgepharma Product Page edgepharma.com/products/dermatology/buffered-lidocaine/, last accessed on Jan. 10, 2020.

Flynn, G. L., *Buffers—pH Control within Pharmaceutical Systems*, J. Parenteral Drug Assoc. (1980) 34(2): 139-162 ("Flynn").

Handbook of Pharmaceutical Excipients, Edetic Acid, 5th Ed., pp. 260-263, Eds. Rowe et al. (2006) ("Handbook").

Hinshaw et al., *Preparation of pH-adjusted Local Anesthetics*, Ophthalmic Surg. (1995) 26(3): 194-199 ("Hinshaw").

Kennedy et al., *The "Ouchless Emergency Department"*, Pediatric Clinics of North America (1999) 46(6): 1215-1247 ("Kennedy").

Larson et al., *Stability of Buffered Lidocaine and Epinephrine Used for Local Anesthesia*, Dermatol. Surg. (1991) 17(5): 411-414 ("Larson").

Long et al., *Taking the 'sting' out of Local Anaesthetics*, Brit. J. Dermatol. (1991) 125(5): 452-455 ("Long").

Maloney et al., *Iontophoretic Administration of Lidocaine Anesthesia in Office Practice: An Appraisal*, J. Dermatol. Surg. Oncol. (1992) 18(11): 937-940 ("Maloney").

Murakami et al., *Buffered Local Anesthetics and Epinephrine Degradation*, J. Dermatol. Surg. (1994) 20(3): 192-195 ("Murakami").

Prescribing information for EMPI's Lidocaine HCl 2% and Epinephrine 1:100,000 Solution for Topical Iontophoretic System ("EMPI's Iontophoretic System").

Robinson et al., Chemical stability of bupivacaine, lidocaine and epinephrine in pH-adjusted solutions, Anaesthesia (2000) 55(9): 853-858 ("Robinson").

Sinnott et al., *On the Mechanism by Which Epinephrine Potentiates Lidocaine's Peripheral Nerve Block*, Anesthesiology (2003) 98(1): 181-188 ("Sinnott")

U.S. patent application Ser. No. 16/381,407, which discloses a ready-to-use liquid formulation comprising: lidocaine hydrochloride in an amount of about 10 mg/mL or about 20 mg/mL; epinephrine hydrochloride in an amount of about 10 mcg/mL, based on epinephrine free base; sodium chloride in an amount of about 7 mg/mL; sodium metabisulfite in an amount of about 5.2 mcg/mL; citric acid in an amount of about 0.2 mg/mL; EDTA sodium in an amount of about 0.2 mg/mL; a sufficient amount of sterile water for injection; and a sufficient amount of a pH adjuster to obtain a pH of about 3.4.

XYLOCAINE® (lidocaine HCl and epinephrine Injection, USP), viz., "Xylocaine® Label" describes a product referred to therein as "Xylocaine MPF with Epinephrine," where MPF refers to Methyl Paraben Free. The Xylocaine® Label states that each mL of the Xylocaine MPF with Epinephrine product contains lidocaine hydrochloride and epinephrine, with 0.5 mg sodium metabisulfite as an anti-oxidant and 0.2 mg citric acid as a stabilizer.

Information disclosed in the related application and the references cited herein is incorporated by reference in its entirety, including to U.S. Provisional Patent Application No. 62/971,348, filed on Feb. 7, 2020. In the event that information incorporated by reference conflicts with the meaning of a term or an expression disclosed herein, the meaning of the term or the expression disclosed herein controls.

The invention claimed is:

1. A ready-to-use liquid formulation comprising:
   lidocaine hydrochloride in an amount of about 5 mg/mL or about 10 mg/mL;
   epinephrine in an amount that ranges from about 10 mcg/mL to about 10.8 mcg/mL;

sodium chloride in an amount of about 6 mg/mL to about 7 mg/mL;
sodium metabisulfite in an amount of about 5 mcg/mL to about 5.6 mcg/mL;
EDTA sodium in an amount of about 0.5 mg/mL to about 0.6 mg/mL;
optionally N-acetyl-L-cysteine in an amount of about 10 mcg/mL to about 13 mcg/mL;
citrate buffer in an amount of about 1 to about 10 mM;
a sufficient amount of sterile water for injection; and
a sufficient amount of a pH adjuster to obtain a pH that ranges from about 6.3 to about 6.5;
wherein the epinephrine content ranges from about 9 mcg/mL to about 9.7 mcg/mL after storage in a light protected environment for about 60 days to about 90 days at a temperature of about 5° C.

2. The ready-to-use liquid formulation of claim 1, wherein N-acetyl-L-cysteine is present in an amount of 10 mcg/mL to about 13 mcg/mL.

3. The ready-to-use liquid formulation of claim 1, wherein epinephrine is present in an amount of about 10 mcg/mL and the sodium metabisulfite in an amount of about 5 mcg/mL.

4. The ready-to-use liquid formulation of claim 1, wherein epinephrine is present in an amount of about 10.5 mcg/mL and the sodium metabisulfite in an amount of about 5.4 mcg/mL.

5. The ready-to-use liquid formulation of claim 1, wherein epinephrine is present in an amount of about 10.8 mcg/mL and the sodium metabisulfite in an amount of about 5.6 mcg/mL.

6. A syringe containing about 3 mL to about 5 mL of the ready-to-use liquid formulation of claim 1.

7. A light-sensitive container comprising the syringe of claim 6, wherein the light sensitive container has light transmission of less than 5% at any wavelength between 290 nm and 450 nm.

8. A ready-to-use liquid formulation consisting of:
lidocaine hydrochloride in an amount of about 5 mg/mL or about 10 mg/mL;
epinephrine in an amount that ranges from about 10 mcg/mL to about 10.8 mcg/mL;
sodium chloride in an amount of about 6 mg/mL to about 7 mg/mL;
sodium metabisulfite in an amount of about 5 mcg/mL to about 5.6 mcg/mL;
EDTA sodium in an amount of about 0.5 mg/mL to about 0.6 mg/mL;
optionally N-acetyl-L-cysteine in an amount of about 10 mcg/mL to about 13 mcg/mL;
citrate buffer in an amount of about 1 to about 10 mM;
a sufficient amount of sterile water for injection; and
a sufficient amount of a pH adjuster to obtain a pH that ranges from about 6.3 to about 6.4;
wherein the epinephrine content ranges from about 9 mcg/mL to about 9.7 mcg/mL after storage in a light protected environment for about 60 days to about 90 days at a temperature of about 5° C.

9. The ready-to-use liquid formulation of claim 8, wherein N-acetyl-L-cysteine is present in an amount of 10 mcg/mL to about 13 mcg/mL.

10. The ready-to-use liquid formulation of claim 8, wherein epinephrine is present in an amount of about 10 mcg/mL and the sodium metabisulfite in an amount of about 5 mcg/mL.

11. The ready-to-use liquid formulation of claim 8, wherein epinephrine is present in an amount of about 10.5 mcg/mL and the sodium metabisulfite in an amount of about 5.4 mcg/mL.

12. The ready-to-use liquid formulation of claim 8, wherein epinephrine is present in an amount of about 10.8 mcg/mL and the sodium metabisulfite in an amount of about 5.6 mcg/mL.

13. A syringe containing about 3 mL to about 5 mL of the ready-to-use liquid formulation of claim 8.

14. A light-sensitive container comprising the syringe of claim 13, wherein the light sensitive container has light transmission of less than 5% at any wavelength between 290 nm and 450 nm.

15. A method for providing procedural analgesia to a patient in need thereof, which comprises:
administering the ready-to-use liquid formulation of claim 1 to the patient.

16. The method of claim 15, wherein the procedural analgesia is associated with a venipuncture, a shave removal, or a punch biopsy.

17. A process for preparing the ready-to-use liquid formulation of claim 1, which comprises:
a) dissolving lidocaine HCl, sodium chloride, sodium citrate, and citric acid in a first container including sterile water for injection to obtain a first solution;
b) dissolving EDTA sodium in second container including sterile water for injection to obtain a second solution and adjusting the pH thereof to a value of from about 2.6 to about 2.7;
c) dissolving epinephrine in the pH-adjusted solution from step b) and optionally adjusting the pH to a value of from pH 2.6 to about 2.7;
d) dissolving epinephrine in the second container of step c);
e) optionally, adjusting the pH of the solution of step c) to a value of from about 2.6 to about 2.7;
f) dissolving sodium metabisulfite and, optionally, N-Acetyl-L-cysteine in the second container of step e);
g) transferring the solution of step f) to the first container;
h) optionally, adjusting the pH of the solution in the first container of step g) to a obtain a pH that ranges from about 6.3 to about 6.5; and
h) filtering the solution of step h) through a 0.22 micron filter.

18. A syringe product containing about 5 mL of the ready-to-use liquid formulation prepared by the process of claim 17.

19. The syringe of claim 18, wherein each of lidocaine and epinephrine has a potency of at least 90% after storage for about 3-months at a temperature of about 25° C.

20. A light-sensitive container comprising the syringe of claim 18, wherein the light-sensitive container has a light transmission of less than 5% at any wavelength between 290 nm and 450 nm.

* * * * *

UNITED STATES PATENT AND TRADEMARK OFFICE
CERTIFICATE OF CORRECTION

| | | |
|---|---|---|
| PATENT NO. | : 11,642,308 B2 | Page 1 of 1 |
| APPLICATION NO. | : 17/147953 | |
| DATED | : May 9, 2023 | |
| INVENTOR(S) | : Leeah et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 324 days.

Signed and Sealed this
Seventh Day of January, 2025

Derrick Brent
*Acting Director of the United States Patent and Trademark Office*